United States Patent [19]

Milgrom

[11] 4,393,879
[45] Jul. 19, 1983

[54] TISSUE-COLLECTING APPARATUS

[75] Inventor: Hyman T. Milgrom, Chicago, Ill.

[73] Assignee: Milex Products, Inc., Chicago, Ill.

[21] Appl. No.: 139,240

[22] Filed: Apr. 11, 1980

[51] Int. Cl.$^3$ .............................................. A61B 10/00
[52] U.S. Cl. ..................................... 128/758; 128/304; 435/284; 435/803; 604/119
[58] Field of Search ............... 128/752, 758, 274, 276, 128/277, 304; 435/284, 292, 803

[56] References Cited

U.S. PATENT DOCUMENTS

| | | | |
|---|---|---|---|
| 1,633,074 | 6/1927 | DeMott | 128/274 X |
| 3,224,434 | 12/1965 | Molomut et al. | 128/749 |
| 3,256,885 | 6/1966 | Higgins et al. | 128/276 |
| 3,610,242 | 10/1971 | Sheridan | 128/276 |
| 3,661,144 | 5/1972 | Jensen et al. | 128/276 X |
| 3,713,443 | 1/1973 | Fertik | 128/276 |
| 3,785,380 | 1/1974 | Brumfield | 128/276 |
| 3,863,624 | 2/1975 | Gram | 128/758 |
| 3,889,657 | 6/1975 | Baumgarten | 128/276 X |
| 3,929,133 | 12/1975 | Ragab | 128/277 |
| 3,946,739 | 3/1976 | Berman et al. | 128/304 |
| 4,006,745 | 2/1977 | Sorensen et al. | 128/276 X |

OTHER PUBLICATIONS

"Milex Tis-U-Trap Uterine Suction Curette".

Primary Examiner—Kyle L. Howell
Assistant Examiner—Angela D. Sykes
Attorney, Agent, or Firm—Wallenstein, Wagner, Hattis, Strampel & Aubel

[57] ABSTRACT

Apparatus for collecting animal or human tissue includes a curette having a passageway therein terminating at the front end of the curette in a tissue-receiving opening formed in a tissue-scraping spoon. The rear end of said curette extends from a housing forming a handle or gripping surface for manipulating the apparatus. The curette passageway communicates with the interior of said housing and to be connected to a source of vacuum for sucking tissue through the tissue-receiving inlet opening of the curette and into the housing. A substantially flat tissue collecting screen is placed at an angle obliquely across the inside of the housing in the path of tissue flow through the housing to form a large tissue collecting area. The screen has a multiplicity of tissue-screening apertures communicating between the curette passageway on one side of the screen and the outlet opening on the other side of the screen. The tissue is collected on the passageway side of the screen and the collected tissue may be observed through the housing which is substantially transparent. The curette housing or handle is manipulated in one hand of the user and a suction regulator is coupled between the housing and the source of vacuum which is adjusted by the second hand of the user.

13 Claims, 6 Drawing Figures

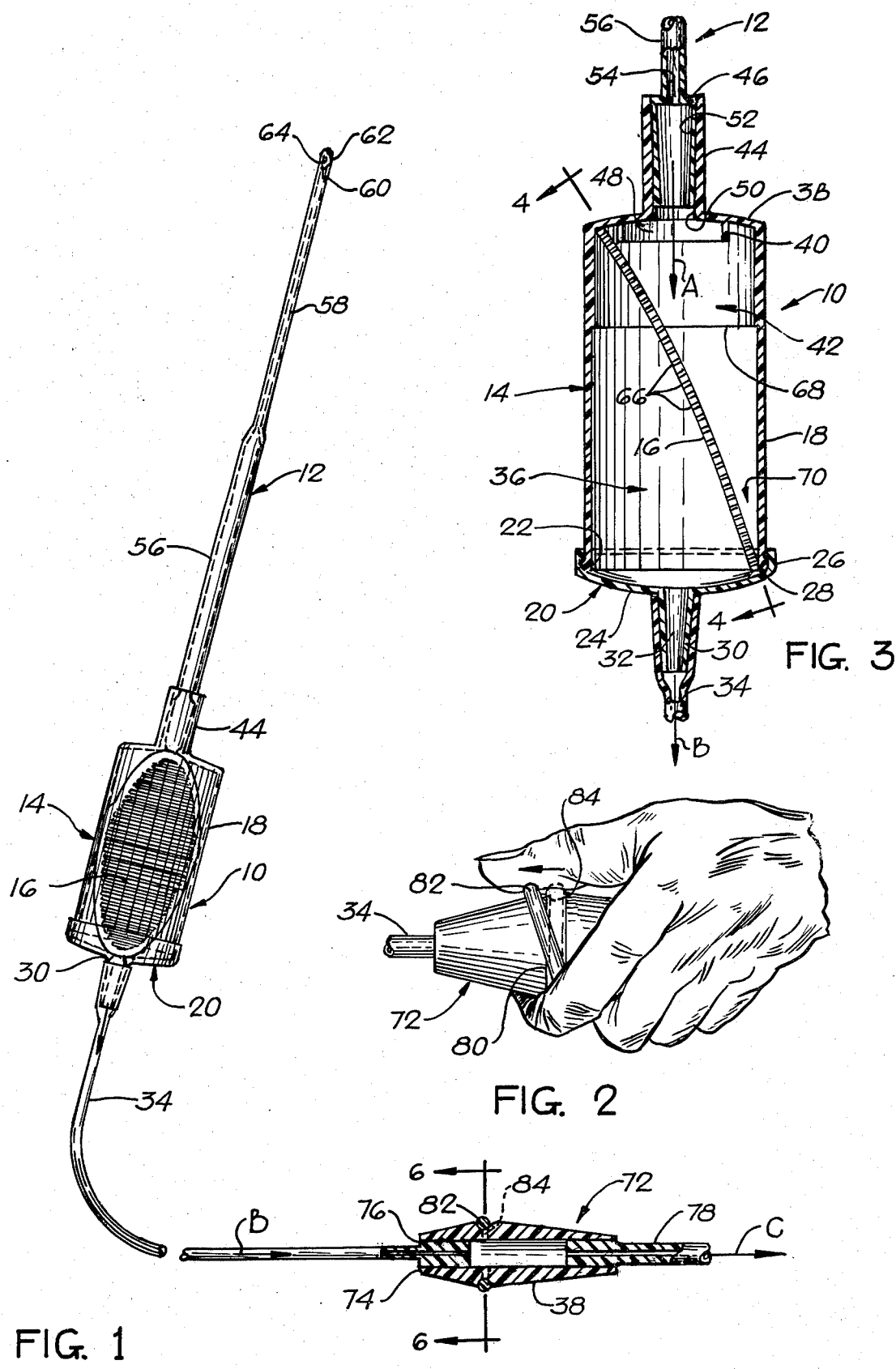

TISSUE-COLLECTING APPARATUS

BACKGROUND OF THE INVENTION

This invention relates to apparatus for collecting tissue, primarily from human beings, for use in uterine cancer screening and endometrial monitoring of patients. Generally, such apparatus includes a curette with a tissue-scraping spoon or the like at one end thereof, which includes a tissue-receiving opening communicating with a passageway extending through the curette and making communication with a housing from which the curette extends. The housing also includes an outlet to be connected to a suction pump which creates a negative pressure, which draws the scraped tissue through the curette and into the housing interior. A screen is placed in the path of flow of the tissue in the housing, which screen collects the tissue. The curette commonly has a suction release opening which removes suction from the end of the curette until the operator closes the hole to establish effective suction at the scraping spoon location at the time when tissue collection is desired. After the tissue is collected by the screen, it is removed from the screen and then examined by a pathologist.

Tissue collection apparatus as described has been heretofore manufactured in a variety of ways. U.S. Pat. No. 3,224,343 to Molomut et al., discloses what is referred to as a cell collection unit having a housing serving as both a handle and a tissue-collecting, filter screen containing housing. The housing is comprised primarily of two parts, one part constituting a curette supporting part which has an enlarged hub or the like at one end having a short internally threaded enlarged portion which receives the externally threaded shank of the other housing part which includes a central passageway communicating between the shank exterior and a rearwardly projecting spout which receives a tube extending to the suction pump. A disk-shaped filter and a washer are sandwiched in a small space between the shank of the latter housing part and the end wall of the short enlarged portion of the former housing part. While the disk-shaped screen described may be satisfactory for collecting a modest quantity of cells or tissue, the collecting area of the screen is so small as to be too small for most tissue collecting applications as described above.

U.S. Pat. No. 3,661,144 to Jensen et al shows a cell collecting apparatus which, while of a more complicated construction than that disclosed in said U.S. Pat. No. 3,224,343, is more adaptable for collecting greater quantities of tissue for examination. In the apparatus disclosed in this patent, the housing for the tissue collection screen is opaque or semi-transparent and comprises a large number of interfitting parts, making the construction thereof a relatively expensive one. Also, it utilizes a cylindrical tissue collection screen of much smaller diameter than the diameter of the housing therefor, the screen dividing the housing interior into an outer annular tissue inlet space and an inner annular space through which liquids and the like which pass through the screen are collected by the suction pump. The annular tissue collecting space on the outside of the screen limits the tissue collecting area of the screen, because of the relatively small diameter of the screen configuration. Also, the tissue collected on the outside of the screen is not readily visible through the housing and must be removed by picking it from the screen surface, which is a very tedious and time-consuming procedure.

U.S. Pat. No. 3,785,380 to Brumfield shows a blood sucker which filters surgical debris from the blood having a filter sleeve similar in construction to U.S. Pat. No. 3,661,144 to Jensen et al.

U.S. Pat. No. 3,889,657 to Baumgarten shows a uterine aspirating curette having a removable tapered or conical specimen collection basket. The material is collected on the inside of the basket and may be difficult to remove from the gauze or mesh basket lining. The basket casing may be made of substantially clear polymeric material to allow visual observation of the amount of collected tissue, but because the tissue is collected on the inside of the basket, it is not readily visible through the housing and basket. The curette has an exposed suction control opening in the basket casing, which casing also serves as the curette handle.

One of the objects of the present invention is to provide tissue collection apparatus which is of a much simpler and more inexpensive construction than that disclosed in the above mentioned patents, while providing a substantial tissue collection area much greater, for example, than that afforded by the disk-shaped screen configuration utilized in the apparatus of said U.S. Pat. No. 3,224,343 to Molomut et al.

A related object of the present invention is to provide tissue collection apparatus as described wherein the construction of the housing and the tissue collection screen contained therein is such as to provide for a very simple assembly procedure and which further permits the ready removal of the screen from the housing and the convenient removal of the tissue from the screen by the pathologist.

A further object of the present invention is to provide a tissue collection apparatus as described which is reliable and is not readily clogged before a maximum desired quantity of tissue is collected therein.

SUMMARY OF THE INVENTION

In accordance with one of the features of the present invention, the tissue collection housing of the apparatus has a uniquely shaped and oriented tissue collection screen which gives a maximum useful collection area for the flat type screen involved. Accordingly, instead of utilizing a circular flat screen configuration, the present invention utilizes a flat most advantageously elongated or oblong screen configuration. The screen wall has a multiplicity of tissue-screening apertures forming a communication between the curette passageway exterior of the screen and a vacuum outlet on the other side of the screen wall.

In the most preferred form of the invention, the oblong screen is of a size to fit diagonally into the interior diameter of a preferably cylindrically-shaped housing in which case the screen has an elliptical shape. The housing also forms a convenient gripping surface or handle for manipulating the apparatus during the insertion of the curette into a body aperture and during the scraping of tissue from the body cavity involved. The diagonal orientation maximizes the tissue collection area of the flat screen while leaving a large space for tissue collection. The size of the housing is preferably one to fit comfortably into the palm of one of the user's hands. The thumb of the second hand having access to one or more suction-breaking holes in a suction regulator, preferably coupled between the housing and the vacuum source.

In accordance with a further feature of the invention, the oblong screen is oriented so that one side faces in the direction of flow of tissue into the housing so that the tissue has a free, unencumbered space in gaining access to the screen and so that the tissue tends to collect as a compacted mass between the housing wall and the screen. Also, the housing is transparent so that the collected tissue is clearly visible in a single mass through the housing without requiring any rotation of the housing. In contrast to this, the tissue collection apparatus of the prior art where the tissue is collected around the entire outer surface of a cylindrical screen, must be rotated to see the entire mass even if the housing is transparent, which it is not in the prior art referred to. Also, in the prior art which utilizes a conical basket in a transparent housing, since the tissue is collected within the basket such tissue is not clearly visible through both the transparent housing and the basket. Additionally, the tissue can be removed in substantially one piece by lifting the screen from the housing. The tissue is then removed from the screen by simply tapping one end of the screen on a horizontal surface or by scraping it from the flat surface. In other words, the incoming tissue is guided by the slanted surface of the screen toward the far end thereof where the tissue is compacted into a single mass. This clumping of the tissue substantially into one piece for facilitating ready removal from the screen without clogging does not take place, for example, where the screen is disk-shaped or is cylindrically-shaped.

In accordance with still another feature of the present invention, the housing of the tissue collection apparatus is provided with a removable wall which confronts one end of the screen so that when the wall is removed, the screen easily can be removed by grasping the readily exposed end of the screen for removal from the housing.

The previously described and other objects, advantages and features of the present invention will become apparent upon making reference to the specification to follow and the drawings.

DESCRIPTION OF DRAWINGS

FIG. 1 is a perspective and partially sectional view of the tissue-collecting and vacuum regulating apparatus constituting the most preferred form of the present invention;

FIG. 2 is an enlarged partial view of a user's hand illustrating the operation of the vacuum regulator of FIG. 1;

FIG. 3 is an enlarged, fragmentary, longitudinal sectional view through the main portion of the apparatus shown in FIG. 1, drawn to scale approximately the actual size thereof;

DESCRIPTION OF EXEMPLARY EMBODIMENT OF THE INVENTION SHOWN IN THE DRAWINGS

Figure 4:
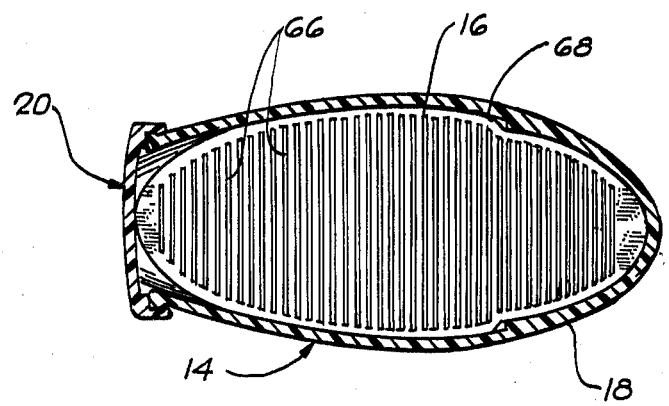
FIG. 4 is a transverse sectional view through the apparatus shown in FIG. 3, taken along section line 4—4 therein.

Referring now more particularly to FIGS. 1 and 3, the apparatus or tissue collector of the invention there shown and generally indicated by reference numeral 10 includes a curette 12. The curette 12 may be a synthetic plastic molded part removably connected to one end of a housing 14. The housing 14 forms a handle for manipulating the apparatus 10 and also a container for an oblong planar tissue-collecting screen 16. The term "oblong" is utilized in its broadest sense and may include rectangular or other forms as well as the preferred elliptical shape. The form of the oblong screen 16 will depend upon the shape of the housing 14, which preferably is generally cylindrical to form an easily grasped handle shape.

The housing 14 includes a main cylindrical body 18 open at its rear end where it is closed by a closure cap 20. The housing body 18 is substantially transparent to visually expose the screen 16 and other contents therein. The main housing body 18 has cylindrical side walls which terminate at the open end thereof in an outwardly extending annular flange 22. The closure cap 20 has a central end wall portion 24 which forms a closure for the main housing body 18 and a flexible axially extending skirt 26 which snaps over the radial housing flange 22 to close the housing body 18. The flange 22 is received within an annular recess 28 in the closure cap skirt 26.

The closure cap 20 has a spout 30 projecting outwardly from the wall portion 24. The spout 30 has a passageway 32 communicating between the exterior of the spout 30 and the inner side of the wall portion 24. A flexible tube 34 removably is secured around the outside of the spout 30 and extends to a vacuum pump or source (not shown). The passageway 32 and hence the tube 34 opens into an inner housing space 36 defined by the inner walls of the housing body 18 and the filtered or downstream side of the screen 16.

The housing body 18 is closed at the end opposite the cap 20 by an end wall 38 from the inner side of which extends a skirt 40 which opens into an inner housing space 42 defined by the inner walls of the housing body 18 and a tissue collecting or unfiltered side of the screen 16. Projecting centrally from the end wall 38 is a spout 44 into which a neck portion 46 of the curette 12 extends in frictional gripping or other secured relation. The skirt 40 defines a cylindrical space 48 therein which communicates between the main housing body space 42 and a smaller space 50 formed in the spout 44. The space 50 communicates with a smaller cylindrical passageway 52 in the neck portion 46 which in turn opens into a passageway 54 in the curette 12.

The curette 12 can have a variety of constructions, but, as illustrated, it includes a relatively large cylindrical portion 56 merging with the neck portion 46 thereof. The cylindrical portion 56 of the curette 12 is shown joining a smaller axially extending cylindrical portion 58 which, in turn, terminates in a collection spoon-forming portion 60. The portion 60 can be inclined at an angle to the longitudinal axis of the portions 56 and 58. The portion 60 includes an inlet opening 62 communicating with the curette passageway 54. A scraping edge 64 formed at the outer edge of the opening 62 aids in scraping tissue from the surface of the body cavity into which the curette 12 is inserted.

As best illustrated in FIGS. 3 and 4, the oblong screen 16 is diagonally engaged in the housing body 18. The screen 16 is sized to engage the inside walls of the body 18 in a substantially fluid tight engagement around the periphery of the screen 16 to divide the body into the upstream and downstream spaces 42 and 36. The screen 16 has a plurality of filtering and tissue collecting apertures 66, preferably in the form of elongate slots. The body 18 has an internal shoulder 68 which does not have any operative function in the described embodiment of the collector 18 and can be eliminated if desired.

Referring to FIGS. 1 through 3, when the vacuum pump is operated fluid and tissue are drawn into the opening 60 and through the passageway 54 into the body space 42 as shown by an arrow "A". The fluid is filtered through the screen apertures 66 and the tissue, if any, is collected between the body walls and the screen 16. The tissue initially will collect adjacent the cap 20 in a portion 70 of the space 42. The tissue thus is gradually collected and compacted without clogging the fluid flow through the screen 16 above the portion 70 which is compacted with tissue. The collected tissue and operation of the filter 16 is observed through the transparent body 18.

The filtered fluid will flow from the space 36 through the passageway 32 into the tubing 34 as shown by the arrow "B". The fluid flow through the collector 10 preferably is regulated by a vacuum regulator 72. The regulator 72 includes a synthetic plastic molded body 74 with a vacuum passageway 76 therethrough. The passageway 76 is sized to frictionally or otherwise engage the tubing 34 and a line 78 in opposite ends thereof. The body 74 has a circumferential groove 80 therearound into which an elastomeric band or ring 82 is engaged. The body 74 has a pair of suction release passageways 84 communicating between the passageway 76 and the groove 80. The body 74 is tapered on both sides of the groove 80 to provide a streamlined shape easily grasped by the forefingers of one hand of the user; positioning the ring 82 therebetween, for manipulation by the user's thumb. The other hand is utilized to manipulate the curette 12 by grasping the housing body 18.

The band 82 is manipulated by the thumb of the user (FIG. 2) to move the band 82 out of the groove 80 opening one or more of the apertures 84 to atmosphere to break the suction in the line 34 and hence in the opening 60. The elastomeric band 82 has a rest position in the groove 80 so that suction normally is applied to the opening 60. The regulator 72 is connected or coupled to the vacuum pump by the line 78. When the pump is operating, the flow C will be constant and the suction flow B is regulated by the user as described above.

Figure 5:
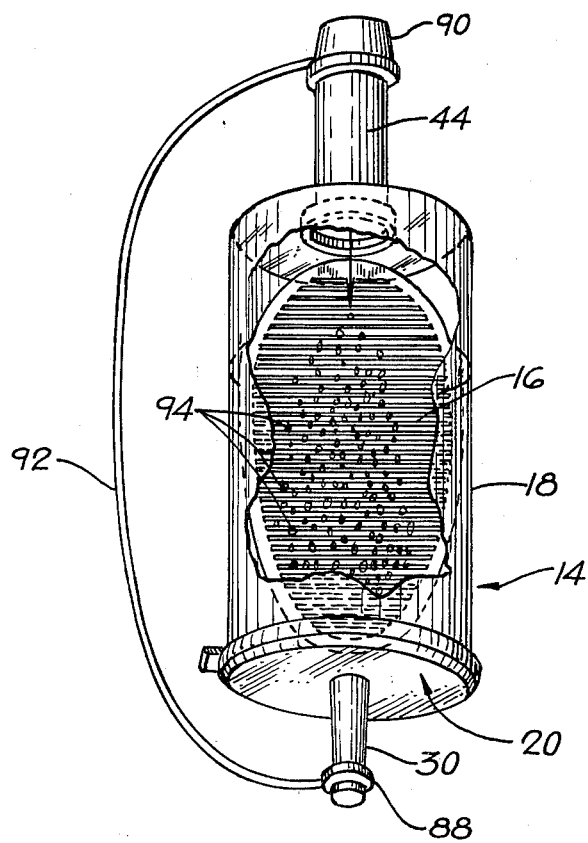
FIG. 5 is a perspective broken away view of the housing with the screen of FIG. 4 therein, after the curette and tubing initially connected to the housing are removed.

When the tissue-collection operation is completed, the curette 12 is removed from the spout 44 of the main housing body 18 and the flexible tube 34 is removed from the spout 30 of the closure cap 20. A pair of closure caps 88 and 90, respectively, then are inserted over the ends of the spouts 30 and 44, as shown in FIG. 5. The closure caps 88 and 90 may have interior projections (not shown) which frictionally extend into the passageways of the spouts 30 and 44 frictionally to hold the caps 88 and 90 in place thereon. The caps 88 and 90 are shown interconnected by a connecting web 92. The web 92 and the closure caps 88 and 90 can be made as a single integral synthetic plastic molded part.

The assembly of the housing 14, the screen 16, tissue 94 collected therein, and the spouts 30 and 44 closed by the caps 88 and 90 is then sent to a pathologist for examination. The pathologist removes the housing closure cap 20 where he can then gain convenient access to the adjacent edge of the screen 16 which he grasps to remove the screen from the housing 14. The screen 16 is tilted away from the adjacent body wall interior and the opposite end may be utilized to scrape any tissue adhering to the body interior away from the body. He then removes the collected tissue 94, which is generally concentrated into a single lump or mass at the adjacent end of the screen in the space 70, by tapping the screen on a suitable surface or by scraping the tissue 94 from the planar screen.

Figure 6:
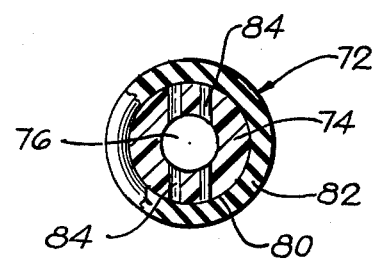
FIG. 6 is an end sectional view through the regulator of FIG. 1 taken along section line 6—6 therein.

The passageways 84 in the regulator body 74 are best illustrated in FIG. 6. The body 74 and the passageways 84 may be formed in various sizes and shapes; however, the pair of peripheral passageways 84 illustrated are preferred. The passageways are aligned substantially parallel and each is spaced so that it passes through opposite edges of the passageway 76. The passageways 84 so formed and aligned provide the most uniform suction breaking areas on the periphery of the groove 80 at the lowest mold cost of the body 74. Passageways 84 passing through the body 74 perpendicularly to one another would provide the maximum spaced suction breaking areas on the groove 80, but would be more expensive to mold.

It should now be apparent that the tissue-collection apparatus of the most advantageous form of the invention just described is of very simple and inexpensive construction. Moreover, the elongate planar screen 16 offers a large screening surface for a given size thereof. Additionally, the tissue is collected on the screen, which can be removed by simply tapping it on a surface or scraping it therefrom, unlike the prior art cylindrical or bag type screen where the removal of the tissue from the screen is a time-consuming and burdensome process.

It should be understood that numerous modifications may be made in the most preferred form of the invention described deviating from the broader aspects thereof.

I claim:

1. In an apparatus for collecting animal or human tissue, said apparatus including a housing having an interior and an exterior, a curette having a tissue-scraping end and a passageway communicating with the housing interior and extending from said housing and terminating at a front end of the curette in a tissue-receiving opening, said housing acting as a handle for manipulating the apparatus, said housing having an outlet opening communicating with the interior of said housing and adapted to be connected to a source of vacuum for sucking tissue through said tissue-receiving opening of said curette and into said housing, the improvement wherein said housing is transparent along at least a portion of one longitudinally extending side thereof, and said housing having a substantially planar tissue collection screen inside said housing in the path of flow of said tissue to be drawn through said curette and into the housing, said screen extending longitudinally and obliquely of said housing for substantially the full length thereof, the screen having a multiplicity of tissue-screening apertures with inlet and outlet sides forming a communication between opposite laterally facing sides of the screen, said apertures being of such a size to catch the tissue being drawn through the housing and screen, the inlet side of the apertures on the side of said screen facing said longitudinally transparent portion of said one side of said housing, and the length of said housing being substantially greater than the lateral dimension thereof so that the obliquely extending screen which extends for substantially the full length of the housing has such a substantial longitudinal component that any tissue collected thereon is readily visible to the user looking laterally into the housing as he grasps the housing to manipulate the apparatus.

2. The tissue-collecting apparatus of claim 1 wherein said housing has cylindrical side walls terminating at the front end of the housing in an end wall from which said curette coaxially extends to form a unit with said housing, said housing forming a handle to manipulate said curette.

3. The tissue-collecting apparatus of claim 1 wherein said housing has a movable end wall adjacent to an end of said planar screen and when the end wall is moved to a housing-opening position by movement of the end wall, said end of said planar screen is within grasp for removing the screen from the housing through the opening.

4. The tissue-collecting apparatus of claim 3 wherein said housing has an abutment wall, said housing movable end wall sandwiches said screen between said movable end wall and an abutment wall on said housing when the end wall is moved to a housing-closing position.

5. The tissue-collecting apparatus of claim 1 wherein there is provided a vacuum regulator separate from said housing, said housing outlet is coupled by tubing to said vacuum regulator, said regulator having a hollow body the interior of which communicates with said tubing, an outlet on said body to be connected to a source of vacuum, said body having at least one vacuum release passageway which is operable or closeable by the user.

6. The tissue-collecting apparatus of claim 5 wherein said regulator body is of a size and shape adapted to be grasped by one hand of a user, said tubing being so short that said housing to be manipulated can be grasped by the other hand of the user as said body is grasped by said one hand.

7. The tissue-collecting apparatus of claim 5 or 6 wherein said regulator body is an elongated tapered substantially cylindrical body having a circumferential groove therearound, said release passageway opening onto said groove, and there is provided elastomeric means engaged in said groove and slidable by the user with the hand adapted to grip said body to cover and uncover said opening.

8. The tissue-collecting apparatus of claims 5, 6 or 7 wherein said body groove includes a plurality of release passageways therein, each passageway opening covered by said elastomeric means.

9. The tissue-collecting apparatus of claims 5, 6 or 7 wherein said body has a vacuum passageway therethrough and a pair of vacuum release passageways passing transversely through said vacuum passageway on opposite sides thereof, each release passageway having an opening on opposite sides of said body, each release passageway opening spaced from one another and covered by said elastomeric means.

10. The tissue-collecting apparatus of claim 5 wherein said housing and said curette are connected together to form a unit, said housing forming a handle adapted to be grasped by one hand of a user to manipulate said curette and the regulator is adapted to be grasped by the other hand of the user to manipulate said elastomeric means to and away from said release opening.

11. The tissue-collecting apparatus of claim 1 wherein the longitudinal dimension of the screen is much greater than its own lateral dimension and the lateral dimension of the housing.

12. The tissue-collecting apparatus of claim 1 wherein said screen extends obliquely across the housing interior and said housing is substantially cylindrical and said screen is elliptical in shape.

13. The tissue-collecting apparatus of claims 1, 2, 3, 9, or 10 wherein said screen extends obliquely across the housing interior.

* * * * *